US00PP35984P2

(12) United States Plant Patent
Koot et al.

(10) Patent No.: US PP35,984 P2
(45) Date of Patent: Jul. 9, 2024

(54) DIPLADENIA PLANT NAMED 'DODIPWHIHA'

(50) Latin Name: *Mandevilla sanderi*
Varietal Denomination: DODIPWHIHA

(71) Applicant: DUMMEN GROUP B.V., De Lier (NL)

(72) Inventors: Arjan Koot, Oeffelt (NL); Josep Escriba, Puerto Lumbreras Murcia (ES)

(73) Assignee: DUMMEN GROUP B.V., De Lier (NL)

( * ) Notice: Subject to any disclaimer, the term of this patent is extended or adjusted under 35 U.S.C. 154(b) by 0 days.

(21) Appl. No.: 18/384,724

(22) Filed: Oct. 27, 2023

(51) Int. Cl.
*A01H 5/02* (2018.01)
*A01H 6/08* (2018.01)

(52) U.S. Cl.
USPC ..... Plt./232
CPC ..... *A01H 6/088* (2018.05)

(58) Field of Classification Search
USPC ..... Plt./232
CPC ..... A01H 6/088; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of Dipladenia plant named 'Dodipwhiha', characterized by its broadly upright plant habit; moderately vigorous growth habit and moderate growth rate; freely branching habit; dense and bushy appearance; glossy dark green-colored leaves; freely flowering habit; white-colored flowers with bright yellow-colored throats; and good garden performance.

2 Drawing Sheets

Figure 1:
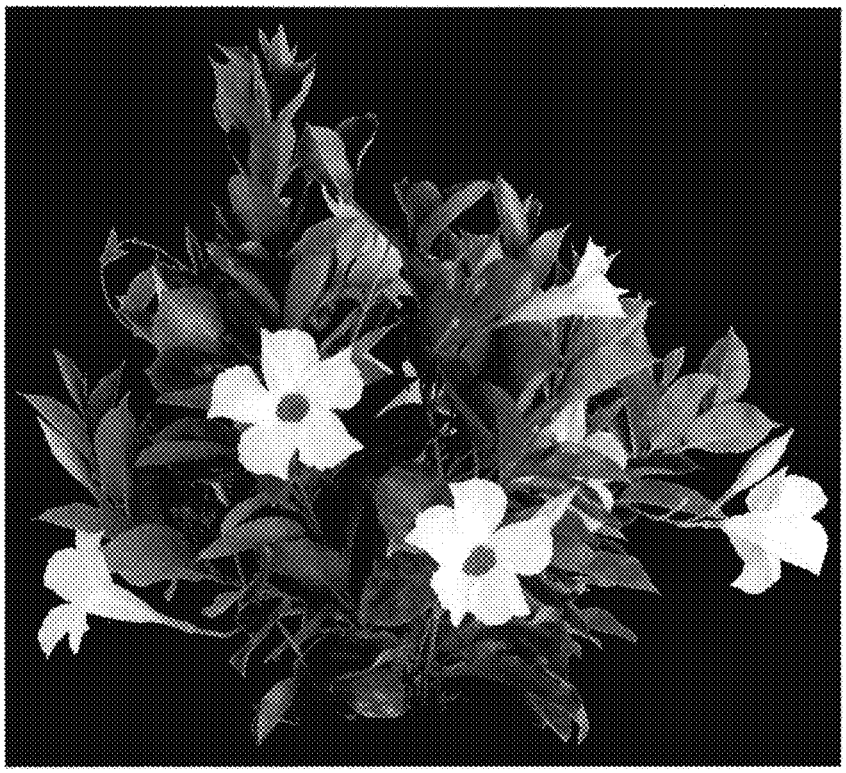

Botanical designation: *Mandevilla sanderi.*
Cultivar denomination: 'DODIPWHIHA'.

BACKGROUND OF THE INVENTION

The present invention relates to a new and distinct cultivar of Dipladenia plant, commonly referred to as *Mandevilla*, botanically known as *Mandevilla sanderi* and hereinafter referred to by the name 'Dodipwhiha' .

The new Dipladenia plant is a product of a planned breeding program conducted by the Inventors in Rheinberg, Germany and Puerto Lumbreras, Murcia, Spain. The objective of the breeding program is to create new freely branching Dipladenia plants that flower freely and have attractive flower colors.

The new Dipladenia plant originated from a cross-pollination conducted by the Inventors in Rheinberg, Germany in September, 2020 of *Mandevilla sanderi* 'Duemarhopi', disclosed in U.S. Plant Pat. No. 24,886, as the female, or seed, parent with a proprietary breeding selection of *Mandevilla sanderi* identified as code number MM07-1002-049, not patented, as the male, or pollen, parent. The new Dipladenia plant was discovered and selected by the Inventors as a single flowering plant from within the progeny of the stated cross-pollination in a controlled greenhouse environment in Puerto Lumbreras, Murcia, Spain in September, 2021.

Asexual reproduction of the new Dipladenia plant by vegetative cuttings in a controlled greenhouse environment in Puerto Lumbreras, Murcia, Spain since November, 2021 has shown that the unique features of this new Dipladenia plant are stable and reproduced true to type in successive generations.

SUMMARY OF THE INVENTION

Plants of the new Dipladenia have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dodipwhiha'. These characteristics in combination distinguish 'Dodipwhiha' as a new and distinct Dipladenia plant:

1. Broadly upright plant habit.
2. Moderately vigorous growth habit and moderate growth rate.
3. Freely branching habit; dense and bushy appearance.
4. Glossy dark green-colored leaves.
5 Freely flowering habit.
6. White-colored flowers with bright yellow-colored throats.
7. Good garden performance.

Plants of the new Dipladenia can be compared to plants of the female parent, 'Duemarhopi'. Plants of the new Dipladenia differ primarily from plants of 'Duemarhopi' in the following characteristics:

1. Leaves of plants of the new Dipladenia are lighter green in color than leaves of plants of 'Duemarhopi'.
2. Plants of the new Dipladenia have larger flowers than plants of 'Duemarhopi'.
3. Flower petals of plants of the new Dipladenia are flatter than flower petals of 'Duemarhopi'.
4. Flowers of plants of the new Dipladenia are white in color whereas flowers of plants of 'Duemarhopi' are red purple in color.

Plants of the new Dipladenia can be compared to plants of the male parent selection. Plants of the new Dipladenia differ primarily from plants of the male parent selection in the following characteristics:

1. Plants of the new Dipladenia have larger leaves than plants of the male parent selection.

2. Plants of the new Dipladenia are more freely flowering than plants of the male parent selection.
3. Plants of the new Dipladenia have smaller flowers than plants of the male parent selection.
4. Flowers of plants of the new Dipladenia are white in color whereas flowers of plants of the male parent selection are red in color.

Plants of the new Dipladenia can also be compared to plants of *Mandevilla sanderi* 'Inmanwhimp', disclosed in U.S. Plant Pat. No. 28,276. In side-by-side comparisons, plants of the new Dipladenia differ primarily from plants 'Inmanwhimp' in the following characteristics:

1. Plants of the new Dipladenia have smaller leaves than plants of 'Inmanwhimp'.
2. Plants of the new Dipladenia are more freely flowering than plants of 'Inmanwhimp'.
3. Flower buds of plants of the new Dipladenia are pale purplish pink in color whereas flower buds of plants of 'Inmanwhimp' are pale yellowish green in color.
4. Plants of the new Dipladenia have smaller flowers than plants of 'Inmanwhimp'.
5. Flower petals of plants of the new Dipladenia are more rounded than flowers petals of plants of 'Inmanwhimp'.

BRIEF DESCRIPTION OF THE PHOTOGRAPHS

The accompanying colored photographs illustrate the overall appearance of the new Dipladenia plant showing the colors as true as it is reasonably possible to obtain in colored reproductions of this type. Colors in the photographs may differ slightly from the color values cited in the detailed botanical description which accurately describe the actual colors of the new Dipladenia plant.

The photograph on the first sheet (FIG. 1) is a side perspective view of a typical flowering plant of 'Dodipwhiha' grown in a container.

Figure 2:
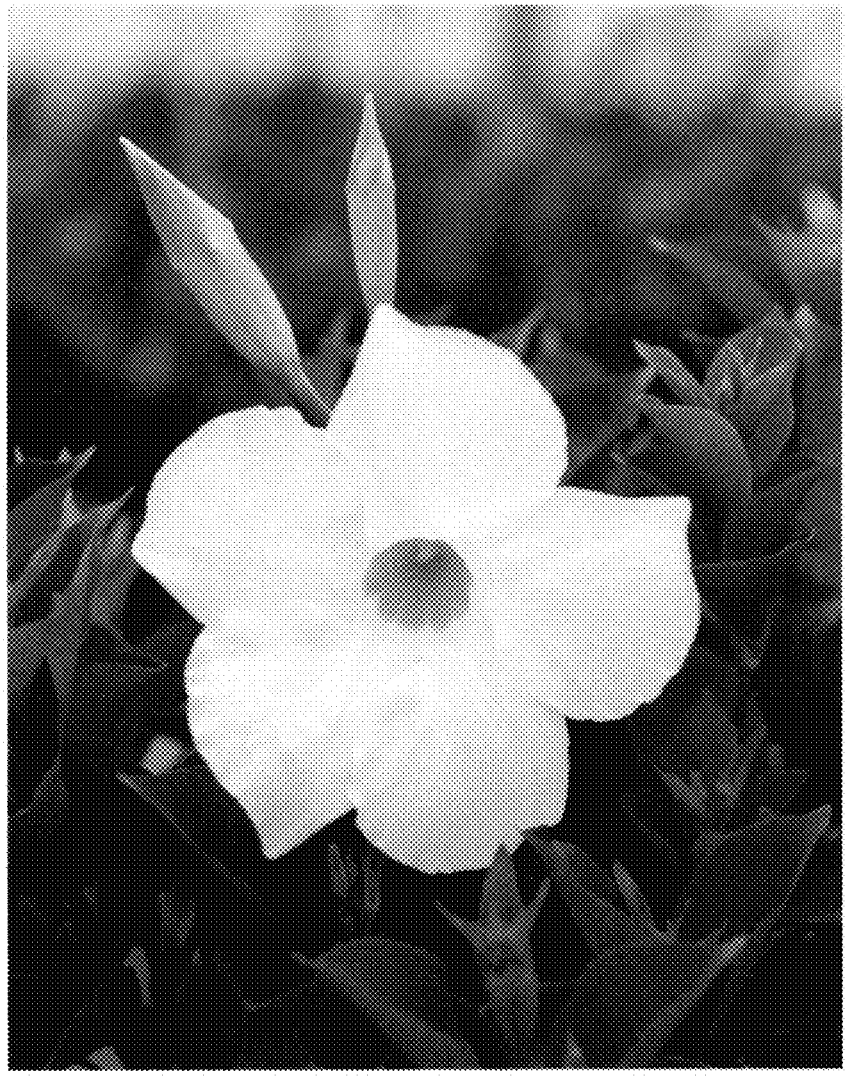

The photograph on the second sheet (FIG. 2) is a close-up view of a typical flower and typical flower buds of 'Dodipwhiha'.

DETAILED BOTANICAL DESCRIPTION

The aforementioned photographs and following observations, measurements and values describe plants grown during the spring in 17-cm containers in a polyethylene-covered greenhouse in Puerto Lumbreras, Murcia, Spain and under cultural practices typical of commercial Dipladenia production. During the production of the plants, day temperatures averaged 21.9 C, night temperatures averaged 11.25 C and light levels averaged 650 watts/m2/h. Plants were two years old when the photographs and description were taken. In the following description, color references are made to The Royal Horticultural Society Colour Chart, 1986 Edition, except where general terms of ordinary dictionary significance are used.

Botanical classification: *Mandevilla sanderi* 'Dodipwhiha'.

Parentage:

*Female, or seed, parent.*—*Mandevilla sanderi* 'Duemarhopi', disclosed in U.S. Plant Pat. No. 24,886.

*Male, or pollen, parent.*—Proprietary breeding selection of *Mandevilla sanderi* identified as code number MM07-1002-049, not patented.

Propagation:

*Type.*—By vegetative cuttings.

*Time to initiate roots, summer.*—About three weeks at temperatures about 30 C.

*Time to initiate roots, winter.*—About three weeks at temperatures about 20 C.

*Time to produce a rooted young plant, summer.*—About 42 days at temperatures about 30 C.

*Time to produce a rooted young plant, winter.*—About 50 days at temperatures about 20 C.

*Root description.*—Thick, fleshy; typically white and brown in color, actual color of the roots is dependent on substrate composition, water quality, fertilizers, substrate temperature and physiological age of roots.

*Rooting habit.*—Moderately freely branching; medium density.

Plant description:

*Plant and growth habit.*—Broadly upright plant habit; moderately vigorous growth habit and moderate growth rate; freely branching habit, dense and bushy appearance.

*Plant height.*—About 60 cm.

*Plant diameter (spread).*—About 60 cm.

*Lateral branch description.*—Branching habit: Freely branching habit, typically about four primary lateral branches each with about three secondary lateral branches per plant; pinching enhances lateral branch development. Length: About 35 cm. Diameter: About 3 mm. Internode length: About 4.5 cm. Strength: Strong. Texture and luster: Smooth, glabrous; semi-glossy; becoming woody with development. Color, developing: Close to 166A. Color, developed: Close to 144A; at the internodes, close to 152C; when woody, close to 165A.

Leaf description:

*Arrangement.*—Opposite, simple.

*Length.*—About 5.6 cm.

*Width.*—About 3.5 cm.

*Shape.*—Elliptical.

*Apex.*—Apiculate.

*Base.*—Rounded.

*Margin.*—Entire.

*Texture and luster, upper and lower surfaces.*—Pubescent; glossy.

*Venation pattern.*—Pinnate.

*Color.*—Developing leaves, upper surface: Close to 144A. Developing leaves, lower surface: Close to 147B. Full expanded leaves, upper surface: Close to 147A; venation, close to 147A. Fully expanded leaves, lower surface: Close to 147B; venation, close to 144D.

*Petioles.*—Length: About 1.1 cm. Diameter: About 1 mm. Strength: Strong. Texture and luster, upper and lower surfaces: Smooth, glabrous; glossy. Color, upper surface: Close to 145A. Color, lower surface: Close to 145B.

Flower description:

*Flower type and flowering habit.*—Star-shaped salverform flowers arranged in terminal and axillary racemes; flowers face mostly upright to outwardly; freely flowering habit with about four flowers per inflorescence and about 112 flower buds and open flowers developing per plant during the flowering season.

*Natural flowering season.*—Plants flower continuously from spring into the autumn in Spain; plants begin flowering about 20 weeks after propagation (dependent on light level).

*Flower longevity on the plant*.—Individual flowers last about four to six days; flowers persistent.

*Fragrance*.—None detected.

*Inflorescence height*.—About 11 cm.

*Inflorescence diameter*.13 About 11 cm.

*Flower buds*.—Length: About 6 cm. Diameter: About 1.2 cm. Shape: Elongated, spindle-shaped. Texture and luster: Smooth, glabrous; glossy. Color: Close to 65D.

*Flowers*.—Appearance: Flared trumpet, corolla fused and five-parted. Diameter: About 6 cm by 6 cm. Depth (length): About 3.5 cm. Throat diameter: About 1.4 cm. Tube length: About 3.5 cm. Tube diameter: About 4 mm.

*Corolla*.—Quantity and arrangement: Five petals arranged in a single whorl; lower portion of the petals are fused into a funnelform tube. Petal length, free lobes: About 3 cm. Petal width, free lobes: About 2.6 cm. Petal shape and appearance: Roughly spatulate. Petal apex: Apiculate. Petal margin: Entire; moderately undulate. Petal texture and luster, upper and lower surfaces: Smooth, glabrous; matte. Throat texture: Smooth, glabrous. Tube texture: Smooth, glabrous. Color: Petal, when opening and fully opened, upper surface: Close to 155D; venation, close to 155D; color does not change with subsequent development. Petal, when opening and fully opened, lower surface: Close to 155D; venation, close to 155D; color does not change with subsequent development. Throat: Close to 15A; venation, close to 15A. Tube: Close to 144B; venation, close to 144B.

*Sepals*.—Quantity and arrangement: Five sepals arranged in a single whorl. Length: About 1.1 cm. Width: About 4 mm. Shape: Ligulate. Apex: Acuminate. Base: Acute. Margin: Entire. Texture and luster, upper and lower surfaces: Smooth, glabrous; semi-glossy. Color: When developing, upper and lower surfaces: Close to 144A. Fully opened, upper and lower surfaces: Close to 170C.

*Peduncles*.—Length: About 1 cm. Diameter: About 2 mm. Strength: Strong. Aspect: About 45 degrees from lateral branch axis. Texture and luster: Smooth, glabrous; matte. Color: Close to 154C.

*Pedicels*.—Length: About 1 cm. Diameter: About 1 mm. Strength: Strong. Aspect: About 45 degrees from peduncle axis. Texture and luster: Smooth, glabrous; matte. Color: Close to 144A.

*Reproductive organs*.—Stamens: Quantity and arrangement: Typically five; basifixed; anthers connivent. Filament length: About 2 mm. Filament color: Close to 8B. Anther size: About 3 mm by 8 mm. Anther shape: Narrowly oblong, elongated. Anther color: Close to 8B. Pollen amount: Moderate. Pollen color: Close to 3C. Pistils: Quantity: Typically one. Pistil length: About 5 mm. Style length: About 2.3 mm. Style color: Close to 1D. Stigma diameter: About 1.8 mm. Stigma shape: Star-shaped. Stigma color: Close to 145A. Ovary color: Close to 1D.

*Seeds and fruits*.—To date, seed and fruit production have not been observed on plants of the new Dipladenia.

Pathogen & pest resistance: To date, plants of the new Dipladenia have not been noted to be resistant to pathogens and pests common to Dipladenia plants.

Garden performance: Plants of the new Dipladenia have been observed to have good garden performance.

It is claimed:

1. A new and distinct Dipladenia plant named 'Dodipwhiha' as illustrated and described.

* * * * *